United States Patent
Kitagawa et al.

(10) Patent No.: US 6,328,963 B1
(45) Date of Patent: Dec. 11, 2001

(54) ANTI-HUMAN MP52 MONOCLONAL ANTIBODY

(75) Inventors: Hiroshi Kitagawa; Tomofumi Jitsukawa, both of Saitama; Hiraku Nakagawa, Kanagawa; Sachiko Yanagisawa, Tokyo, all of (JP)

(73) Assignee: Hoechst Marion Roussel (FR)

( * ) Notice: Subject to any disclaimer, the term of this patent is extended or adjusted under 35 U.S.C. 154(b) by 0 days.

(21) Appl. No.: 09/180,700

(22) PCT Filed: May 13, 1997

(86) PCT No.: PCT/JP97/01603

§ 371 Date: Dec. 23, 1998

§ 102(e) Date: Dec. 23, 1998

(87) PCT Pub. No.: WO97/43408

PCT Pub. Date: Nov. 20, 1997

(30) Foreign Application Priority Data

May 13, 1996 (JP) .................................................. 8-141137
May 7, 1997 (JP) .................................................. 9-131631

(51) Int. Cl.[7] ........................ A61K 39/395; C12P 21/04; G01N 33/53; C07K 16/00
(52) U.S. Cl. ................................... 424/141.1; 424/145.1; 424/158.1; 435/70.1; 435/70.21; 435/71.1; 436/547; 436/548; 530/388.1; 530/388.23; 530/391.1
(58) Field of Search ............................... 424/141.1, 145.1, 424/158.1; 435/70.1, 70.21, 71.1; 436/547, 548; 530/388.1, 388.23, 391.1

(56) References Cited

FOREIGN PATENT DOCUMENTS

WO 93/16099    8/1993   (WO) .
WO 94/15949    7/1994   (WO) .

OTHER PUBLICATIONS

G. Hotten et al, "Cloning . . . Factor 5", Biochem. Biophys. Res. Commun. (1994), vol. 204, pp. 646–652.
Storm et al, "Limb Alterations . . . Superfamily", Nature (1994), vol. 368, pp. 639–643.
Lucas et al, "The Autocrine . . . Activation", J. Immunol. (1990), vol. 145, pp. 1415–1422.

*Primary Examiner*—Rodney P. Swartz
(74) *Attorney, Agent, or Firm*—Bierman, Muserlian and Lucas (57) ABSTRACT

A mouse anti-human MP52 monoclonal antibody which binds to dimeric human MP52 but not to monomeric human MP52. This mouse monoclonal antibody comprising IgG and having a high specificity can be obtained by sensitizing mice with human MP52 (CHO-MP52) produced in CHO cells and human MP52 (rhMP52) produced in *escherichia coli*. This antibody is useful in, for example, purifying or assaying human MP52 produced b genetic engineering techniques.

13 Claims, 5 Drawing Sheets

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 357 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
             (A) ORGANISM: Homo sapiens (ix) FEATURE:
             (A) NAME/KEY: CDS
             (B) LOCATION:1..357
             (D) OTHER INFORMATION:/note= "Relevant amino acid
                 residues in SEQ ID No 1 from 1 to 119 in WO
                 95/04819"

(x) PUBLICATION INFORMATION:
             (A) AUTHORS: HOTTEN, Gertrud
                          NEIDHARDT, Helge
                          PAULISTA, Michael
             (B) TITLE: New growth/differentiation factor of the
                 tgf-beta familie.
             (H) DOCUMENT NUMBER: WO 95/04819
             (J) PUBLICATION DATE: 16-FEB-1995
             (K) RELEVANT RESIDUES IN SEQ ID NO: 1: FROM 1 TO 357

(xi) SEQUENCE DESCRIPTION: SEQ ID NO: 1:

```
CCA CTG GCC ACT CGC CAG GGC AAG CGA CCC AGC AAG AAC CTT AAG GCT      48
Pro Leu Ala Thr Arg Gln Gly Lys Arg Pro Ser Lys Asn Leu Lys Ala
 1               5                  10                  15

CGC TGC AGT CGG AAG GCA CTG CAT GTC AAC TTC AAG GAC ATG GGC TGG      96
Arg Cys Ser Arg Lys Ala Leu His Val Asn Phe Lys Asp Met Gly Trp
             20                  25                  30

GAC GAC TGG ATC ATC GCA CCC CTT GAG TAC GAG GCT TTC CAC TGC GAG     144
Asp Asp Trp Ile Ile Ala Pro Leu Glu Tyr Glu Ala Phe His Cys Glu
         35                  40                  45

GGG CTG TGC GAG TTC CCA TTG CGC TCC CAC CTG GAG CCC ACG AAT CAT     192
Gly Leu Cys Glu Phe Pro Leu Arg Ser His Leu Glu Pro Thr Asn His
 50                  55                  60

GCA GTC ATC CAG ACC CTG ATG AAC TCC ATG GAC CCC GAG TCC ACA CCA     240
Ala Val Ile Gln Thr Leu Met Asn Ser Met Asp Pro Glu Ser Thr Pro
 65                  70                  75                  80

CCC ACC TGC TGT GTG CCC ACG CGA CTG AGT CCC ATC AGC ATC CTC TTC     288
Pro Thr Cys Cys Val Pro Thr Arg Leu Ser Pro Ile Ser Ile Leu Phe
             85                  90                  95

ATT GAC TCT GCC AAC AAC GTG GTG TAT AAG CAG TAT GAG GAC ATG GTC     336
Ile Asp Ser Ala Asn Asn Val Val Tyr Lys Gln Tyr Glu Asp Met Val
        100                 105                 110

GTG GAG TCG TGT GGC TGC AGG                                         357
Val Glu Ser Cys Gly Cys Arg
        115
```

(2) INFORMATION FOR SEQ ID NO: 2:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE"

(ix) FEATURE:
            (A) NAME/KEY: misc_feature
            (B) LOCATION:1..27
            (D) OTHER INFORMATION:/note= "PCR upstream primer of
                MP52 mature type"

(xi) SEQUENCE DESCRIPTION: SEQ ID NO: 2:

ATAATGCCAC TAGCAACTCG TCAGGGC                                        27

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "OLIGONUCLEOTIDE"

(ix) FEATURE:
        (A) NAME/KEY: misc_feature
        (B) LOCATION:complement (1..26)
        (D) OTHER INFORMATION:/note= "PCR downstream primer of
            MP52 mature type"

(xi) SEQUENCE DESCRIPTION: SEQ ID NO: 3:

CGTCGACTAC CTGCAGCCAC ACGACT                                            26

(2) INFORMATION FOR SEQ ID NO: 4:

(i) SEQUENCE CHARACTERISTICS:
        (A) LENGTH: 2703 base pairs
        (B) TYPE: nucleic acid
        (C) STRANDEDNESS: single
        (D) TOPOLOGY: linear     (ii) MOLECULE TYPE: cDNA     (vi) ORIGINAL SOURCE:
        (A) ORGANISM: Homo sapiens     (ix) FEATURE:
        (A) NAME/KEY: CDS
        (B) LOCATION:640..2142
        (D) OTHER INFORMATION:/note= "Bone morphogenetic protein
            MP52"

(ix) FEATURE:
        (A) NAME/KEY: mat_peptide
        (B) LOCATION: 1783..2142

(ix) FEATURE:
        (A) NAME/KEY: sig_peptide
        (B) LOCATION:640..720

(x) PUBLICATION INFORMATION:
        (A) AUTHORS: HOTTEN, Gertrud
            NEIDHARDT, Helge
            PAULISTA, Michael
        (B) TITLE: New growth/differentiation factor of the
            tgf-beta familie.
        (H) DOCUMENT NUMBER: WO 95/04819
        (J) PUBLICATION DATE: 16-FEB-1995

(xi) SEQUENCE DESCRIPTION: SEQ ID NO: 4:

CCATGGCCTC GAAAGGGCAG CGGTGATTTT TTTCACATAA ATATATCGCA CTTAAATGAG    60

TTTAGACAGC ATGACATCAG AGAGTAATTA AATTGGTTTG GGTTGGAATT CCGTTTCCAA   120

TTCCTGAGTT CAGGTTTGTA AAAGATTTTT CTGAGCACCT GCAGGCCTGT GAGTGTGTGT   180

GTGTGTGTGT GTGTGTGTGT GTGTGTGTGA AGTATTTTCA CTGGAAAGGA TTCAAAACTA   240

GGGGGAAAAA AAAACTGGAG CACACAGGCA GCATTACGCC ATTCTTCCTT CTTGGAAAAA   300

TCCCTCAGCC TTATACAAGC CTCCTTCAAG CCCTCAGTCA GTTGTGCAGG AGAAAGGGGG   360

CGGTTGGCTT TCTCCTTTCA AGAACGAGTT ATTTTCAGCT GCTGACTGGA GACGGTGCAC   420

GTCTGGATAC GAGAGCATTT CCACTATGGG ACTGGATACA AACACACACC CGGCAGACTT   480

CAAGAGTCTC AGACTGAGGA GAAAGCCTTT CCTTCTGCTG CTACTGCTGC TGCCGCTGCT   540

```
                                                                        -continued

TTTGAAAGTC CACTCCTTTC ATGGTTTTTC CTGCCAAACC AGAGGCACCT TTGCTGCTGC           600

CGCTGTTCTC TTTGGTGTCA TTCAGCGGCT GGCCAGAGG ATG AGA CTC CCC AAA             654
                                            Met Arg Leu Pro Lys
                                            -27     -25

CTC CTC ACT TTC TTG CTT TGG TAC CTG GCT TGG CTG GAC CTG GAA TTC            702
Leu Leu Thr Phe Leu Leu Trp Tyr Leu Ala Trp Leu Asp Leu Glu Phe
            -20             -15             -10

ATC TGC ACT GTG TTG GGT GCC CCT GAC TTG GGC CAG AGA CCC CAG GGG            750
Ile Cys Thr Val Leu Gly Ala Pro Asp Leu Gly Gln Arg Pro Gln Gly
    -5               1               5                       10

ACC AGG CCA GGA TTG GCC AAA GCA GAG GCC AAG GAG AGG CCC CCC CTG            798
Thr Arg Pro Gly Leu Ala Lys Ala Glu Ala Lys Glu Arg Pro Pro Leu
                 15              20              25

GCC CGG AAC GTC TTC AGG CCA GGG GGT CAC AGC TAT GGT GGG GGG GCC            846
Ala Arg Asn Val Phe Arg Pro Gly Gly His Ser Tyr Gly Gly Gly Ala
             30              35              40

ACC AAT GCC AAT GCC AGG GCA AAG GGA GGC ACC GGG CAG ACA GGA GGC            894
Thr Asn Ala Asn Ala Arg Ala Lys Gly Gly Thr Gly Gln Thr Gly Gly
             45              50              55

CTG ACA CAG CCC AAG AAG GAT GAA CCC AAA AAG CTG CCC CCC AGA CCG            942
Leu Thr Gln Pro Lys Lys Asp Glu Pro Lys Lys Leu Pro Pro Arg Pro
        60              65              70

GGC GGC CCT GAA CCC AAG CCA GGA CAC CCT CCC CAA ACA AGG CAG GCT            990
Gly Gly Pro Glu Pro Lys Pro Gly His Pro Pro Gln Thr Arg Gln Ala
75              80              85                      90

ACA GCC CGG ACT GTG ACC CCA AAA GGA CAG CTT CCC GGA GGC AAG GCA           1038
Thr Ala Arg Thr Val Thr Pro Lys Gly Gln Leu Pro Gly Gly Lys Ala
                 95             100             105

CCC CCA AAA GCA GGA TCT GTC CCC AGC TCC TTC CTG CTG AAG AAG GCC           1086
Pro Pro Lys Ala Gly Ser Val Pro Ser Ser Phe Leu Leu Lys Lys Ala
            110             115             120

AGG GAG CCC GGG CCC CCA CGA GAG CCC AAG GAG CCG TTT CGC CCA CCC           1134
Arg Glu Pro Gly Pro Pro Arg Glu Pro Lys Glu Pro Phe Arg Pro Pro
        125             130             135

CCC ATC ACA CCC CAC GAG TAC ATG CTC TCG CTG TAC AGG ACG CTG TCC           1182
Pro Ile Thr Pro His Glu Tyr Met Leu Ser Leu Tyr Arg Thr Leu Ser
    140             145             150

GAT GCT GAC AGA AAG GGA GGC AAC AGC AGC GTG AAG TTG GAG GCT GGC           1230
Asp Ala Asp Arg Lys Gly Gly Asn Ser Ser Val Lys Leu Glu Ala Gly
155             160             165                     170

CTG GCC AAC ACC ATC ACC AGC TTT ATT GAC AAA GGG CAA GAT GAC CGA           1278
Leu Ala Asn Thr Ile Thr Ser Phe Ile Asp Lys Gly Gln Asp Asp Arg
                175             180             185

GGT CCC GTG GTC AGG AAG CAG AGG TAC GTG TTT GAC ATT AGT GCC CTG           1326
Gly Pro Val Val Arg Lys Gln Arg Tyr Val Phe Asp Ile Ser Ala Leu
            190             195             200

GAG AAG GAT GGG CTG CTG GGG GCC GAG CTG CGG ATC TTG CGG AAG AAG           1374
Glu Lys Asp Gly Leu Leu Gly Ala Glu Leu Arg Ile Leu Arg Lys Lys
        205             210             215

CCC TCG GAC ACG GCC AAG CCA GCG GCC CCC GGA GGC GGG CGG GCT GCC           1422
Pro Ser Asp Thr Ala Lys Pro Ala Ala Pro Gly Gly Gly Arg Ala Ala
    220             225             230

CAG CTG AAG CTG TCC AGC TGC CCC AGC GGC CGG CAG CCG GCC TCC TTG           1470
Gln Leu Lys Leu Ser Ser Cys Pro Ser Gly Arg Gln Pro Ala Ser Leu
235             240             245             250

CTG GAT GTG CGC TCC GTG CCA GGC CTG GAC GGA TCT GGC TGG GAG GTG           1518
Leu Asp Val Arg Ser Val Pro Gly Leu Asp Gly Ser Gly Trp Glu Val
            255             260             265

TTC GAC ATC TGG AAG CTC TTC CGA AAC TTT AAG AAC TCG GCC CAG CTG           1566
```

```
                                                                           -continued Phe Asp Ile Trp Lys Leu Phe Arg Asn Phe Lys Asn Ser Ala Gln Leu
            270                 275                 280

TGC CTG GAG CTG GAG GCC TGG GAA CGG GGC AGG GCC GTG GAC CTC CGT      1614
Cys Leu Glu Leu Glu Ala Trp Glu Arg Gly Arg Ala Val Asp Leu Arg
            285                 290                 295

GGC CTG GGC TTC GAC CGC GCC GCC CGG CAG GTC CAC GAG AAG GCC CTG      1662
Gly Leu Gly Phe Asp Arg Ala Ala Arg Gln Val His Glu Lys Ala Leu
300                 305                 310

TTC CTG GTG TTT GGC CGC ACC AAG AAA CGG GAC CTG TTC TTT AAT GAG      1710
Phe Leu Val Phe Gly Arg Thr Lys Lys Arg Asp Leu Phe Phe Asn Glu
315                 320                 325                 330

ATT AAG GCC CGC TCT GGC CAG GAC GAT AAG ACC GTG TAT GAG TAC CTG      1758
Ile Lys Ala Arg Ser Gly Gln Asp Asp Lys Thr Val Tyr Glu Tyr Leu
            335                 340                 345

TTC AGC CAG CGG CGA AAA CGG CGG GCC CCA CTG GCC ACT CGC CAG GGC      1806
Phe Ser Gln Arg Arg Lys Arg Arg Ala Pro Leu Ala Thr Arg Gln Gly
            350                 355                 360

AAG CGA CCC AGC AAG AAC CTT AAG GCT CGC TGC AGT CGG AAG GCA CTG      1854
Lys Arg Pro Ser Lys Asn Leu Lys Ala Arg Cys Ser Arg Lys Ala Leu
            365                 370                 375

CAT GTC AAC TTC AAG GAC ATG GGC TGG GAC GAC TGG ATC ATC GCA CCC      1902
His Val Asn Phe Lys Asp Met Gly Trp Asp Asp Trp Ile Ile Ala Pro
            380                 385                 390

CTT GAG TAC GAG GCT TTC CAC TGC GAG GGG CTG TGC GAG TTC CCA TTG      1950
Leu Glu Tyr Glu Ala Phe His Cys Glu Gly Leu Cys Glu Phe Pro Leu
395                 400                 405                 410

CGC TCC CAC CTG GAG CCC ACG AAT CAT GCA GTC ATC CAG ACC CTG ATG      1998
Arg Ser His Leu Glu Pro Thr Asn His Ala Val Ile Gln Thr Leu Met
            415                 420                 425

AAC TCC ATG GAC CCC GAG TCC ACA CCA CCC ACC TGC TGT GTG CCC ACG      2046
Asn Ser Met Asp Pro Glu Ser Thr Pro Pro Thr Cys Cys Val Pro Thr
            430                 435                 440

CGG CTG AGT CCC ATC AGC ATC CTC TTC ATT GAC TCT GCC AAC AAC GTG      2094
Arg Leu Ser Pro Ile Ser Ile Leu Phe Ile Asp Ser Ala Asn Asn Val
            445                 450                 455

GTG TAT AAG CAG TAT GAG GAC ATG GTC GTG GAG TCG TGT GGC TGC AGG      2142
Val Tyr Lys Gln Tyr Glu Asp Met Val Val Glu Ser Cys Gly Cys Arg
            460                 465                 470

TAGCAGCACT GGCCCTCTGT CTTCCTGGGT GGCACATCCC AAGAGCCCCT TCCTGCACTC    2202

CTGGAATCAC AGAGGGGTCA GGAAGCTGTG GCAGGAGCAT CTACACAGCT TGGGTGAAAG    2262

GGGATTCCAA TAAGCTTGCT CGCTCTCTGA GTGTGACTTG GGCTAAAGGC CCCCTTTTAT    2322

CCACAAGTTC CCCTGGCTGA GGATTGCTGC CCGTCTGCTG ATGTGACCAG TGGCAGGCAC    2382

AGGTCCAGGG AGACAGACTC TGAATGGGAC TGAGTCCCAG GAAACAGTGC TTTCCGATGA    2442

GACTCAGCCC ACCATTTCTC CTCACCTGGG CCTTCTCAGC CTCTGGACTC TCCTAAGCAC    2502

CTCTCAGGAG AGCCACAGGT GCCACTGCCT CCTCAAATCA CATTTGTGCC TGGTGACTTC    2562

CTGTCCCTGG GACAGTTGAG AAGCTGACTG GGCAAGAGTG GGAGAGAAGA GGAGAGGGCT    2622

TGGATAGAGT TGAGGAGTGT GAGGCTGTTA GACTGTTAGA TTTAAATGTA TATTGATGAG    2682

ATAAAAAGCA AAACTGTGCC T                                              2703
```

ANTI-HUMAN MP52 MONOCLONAL ANTIBODY

FIELD OF THE INVENTION

This invention relates to a novel anti-human MP52 mouse monoclonal antibody. More specifically, this invention relates to an anti-human MP52 mouse monoclonal antibody which is capable of binding to a dimeric human MP52, but not to a monomeric human MP52.

Moreover, this invention relates to a hybridoma capable of producing an anti-human MP52 mouse monoclonal antibody described above and the use thereof.

BACKGROUND OF THE INVENTION

Human MP52 was first isolated for its CDNA as an osteogenetic factor belonging to TGF-β gene superfamily in 1994 (Biochem. Biophy. Res. Comm., Vol. 204, No. 2, 1994). Human MP52 is considered as a protein having 120 amino acid residues with alanine at the N-terminus, and its amino acid sequence is reported in WO93/16099 and WO95/04819. It is evident from various animal tests that MP52 is involved in osteogenesis similar to other osteogenetic factors. However, there have been left many unknown points in reference to by what MP52 is directly induced in osteogenesis and by what mechanism osteogenesis is performed, and there have been issued only a few reports thereon.

In addition, mouse MP52 is different from human MP52 in only one of the amino acid sequence at the N-terminal site, and thus MP52 is derived from a gene firmly preserved over species so that it is not that easy to obtain an antibody to human MP52 from a mouse, although it was reported in WO93/16099 that a mouse monoclonal antibody became available.

DISCLOSURE OF THE INVENTION

It is an object of the present invention to provide an anti-human MP52 mouse monoclonal antibody which is capable of binding to a dimeric human MP52, but not to a monomeric human MP52.

There has been attempted to produce human MP52 by means of genetic engineering. In purifying human MP52 produced by incubation of host cells having integrated therein cDNA encoding human MP52, it is found effective to purify the human MP52 using a monoclonal antibody capable of specifically binding to human MP52. More specifically, a monoclonal antibody specific to human MP52 is borne on a carrier, and contacted with a roughly purified MP52 to isolate human MP52 by binding and then human MP52 is separated. In this case, in order to isolate the active dimeric MP52, it is apparently advantageous to employ such a monoclonal antibody that is capable of binding specifically to a dimeric human MP52.

The monoclonal antibody to human MP52 can be used for quantitation of human MP52. The human MP52 quantitation is useful for elucidation of MP52-inducing factors and studies on osteogenesis mechanism. In this case, a dimeric MP52 may be catabolized in a living body to an inactivated monomer or fragments thereof. The active dimeric MP52 solely can be detected using a monoclonal antibody specifically binding to a dimeric MP52.

Moreover, the invention provides an antibody which is capable of binding to a biologically active site of human MP52. That is to say, there is provided an anti-human MP52 mouse monoclonal antibody which may prevent the binding between human MP52 and the receptor thereof. The antibody of the invention specifically recognizes a high-order structure of human MP52 and binds to human MP52 at the active site thereof to inhibit the activity thereof. Since the antibody recognizes an active site of human MP52, it does not recognize any inactive portions even in the dimeric MP52. This is evidently advantageous when applied to its separation or assay.

The mouse monoclonal antibody of this invention can be produced by the following steps in accordance with a well-known process for producing a monoclonal antibody:

(1) sensitizing mice with human MP52 as an immunogen over a prolonged period of time, (2) performing cell fusion between spleen cells of sensitized mice and mouse myeloma cells, (3) screening the hybridoma producing a monoclonal antibody to human MP52 from the resulting hybridoma, (4) cloning the desired antibody-producing hybridoma, (5) performing large scale culture of the cloned cells to produce an antibody, or transplanting the cloned cells into mice intraperitoneally to produce an antibody, and (6) separating and purifying the antibody contained in culture supernatant or the ascites.

The above steps will be explained in more details hereinafter.

In the preparation of immunosensitized mice in the step (1), a solution of human MP52 in 10 mM aqueous hydrochloric acid is admixed and emulsified with a complete Freund adjuvant (CFA) and the resultant emulsion is administered to mice intraperitoneally several times at a frequency of 4 times per 4 months. A content of the MP52 is suitably from 10 μg to 100 μg. After about one month interval from the administration, a solution of 10–100 μg of human MP52 emulsified similarly with an incomplete Freund adjuvant (IFA) is administered to the mice intraperitoneally. Desirably, the mice which have been continuously sensitized with human MP52 together with the adjuvants are given subcutaneously, after a further interval of one to two months, 10–100 μg of human MP52 without any adjuvant, and, a few days before the cell fusion, 10–100 μg of human MP52 is further administered intravenously to the mice at the tail vein.

Production of human MP52 has been attempted by using an expression vector having integrated therein the cDNA encoding said human MP52 and animal cells such as CHO cells and bacteria such as Escherichia coli as a host. The present inventors have attempted to produce a monoclonal antibody using as a sensitizing antigen human MP52 produced in CHO cells (hereinafter referred to as CHO-MP52) [Human MP52-producing animal cell line MC-2 has been deposited in the National Institute of Bioscience and Human-Technology, Agency of Industrial Science and Technology (1–3, Higashi 1-chome, Tsukuba-shi, Ibaraki, Japan) with the international deposit number FERM BP-5142.] and human MP52 produced by Escherichia coli (hereinafter referred to as rhMP52) [An expression vector for human MP52 has been deposited in the National Institute of Bioscience and Human-Technology, Agency of Industrial Science and Technology (1-3, Higashi 1-chome, Tsukuba-shi, Ibaraki, Japan) with the international deposit number FERM BP-5499.], respectively. The resulting antibodies were all IgMs having a lower specificity. However, the inventors have succeeded in producing a monoclonal antibody having a higher specificity by using both CHO-MP52 and rhMP52 as a sensitizing antigen.

In the cell fusion of the step (2), the spleen of the sufficiently immunosensitized mouse In the step (1) is first excised and then a suspension of the spleen cells is prepared in a conventional manner. Next, a mixture of the resulting spleen cells and mouse myeloma cells is subjected to cell fusion treatment using warm polyethylene glycol. After the treatment, non-fused cells are removed from the cell mixture using a medium containing fetal calf serum (FCS) and HAT [hypoxanthine (H), aminopterine (A) and thymidine (T)]. The resulting mixture is poured portionwise into a 96-well plate at a low concentration (a concentration at which one clone is capable of being propagated in one well) and after one week a supernatant in the well where propagation has been confirmed is recovered.

The assay of an anti-human MP52 antibody produced in the supernatant of the step (3) may be performed by using a plate with 96 wells coated with human MP52 used as an immunogen according to a conventional ELISA method. In order to select the antibody to human MP52 which is not bound to a monomeric human MP52, but is bound to a dimeric human MP52, two ELISA methods are combined wherein 1) untreated (nonreduced) dimeric human MP52 (D-rhMP52) and 2) reduced monomeric human MP52 (M-rhMP52) are used. In this case, the monomer molecule in a reduced state may easily form the corresponding dimer when coated on the plate and therefore, the monomer to be used for coating is sulfonated in a conventional manner to avoid reconstruction of the dimer molecule. Further, specific reactivity of the antibody with the monomeric human MP52 and dimeric human MP52 is confirmed according to Western blotting method. As a result, a monoclonal antibody which reacts strongly either to M-rhMP52 or D-rhMP52 and a monoclonal antibody which reacts to both were obtained.

The specificity of the monoclonal antibody can be confirmed by Western blotting method. Namely, rhMP52s under the non-reducing conditions (D-rhMP) and under the reducing conditions (M-rhMP) are subjected to SDS-PAGE, and then transferred to a nitrocellulose membrane by the standard method. The nitrocellulose membrane carrying the transferred rhMP52 thereon was incubated in the culture supernatant containing a monoclonal antibody, it was detected by a HRPO-labelled rabbit immunoglobulin. The results were in agreement with those of the primary screening with the ELISA.

In addition, the specificity can be confirmed by TGF-β2 and BMP-2 to which human MP52 resembles as an antigen for the ELISA in the same manner. All the monoclonal antibodies obtained failed to react with the TGF-β2 and the BMP-2.

The cloning procedure in the step (4) is performed by portionwise pouring at 0.5 cell per one well according to a limiting dilution method.

The step (5) is performed according to a well-known method. As compared with the case where a cloned hybridoma is incubated in a conventional medium and an antibody is obtained from the cultured supernatant, the antibody may be recovered at several hundreds to several thousands-fold concentrations by intraperitoneal transplantation of the hybridoma in mice.

The step (6) is performed according to a well-known method. There may be applied affinity chromatography using protein A or protein G.

The characteristics of the present monoclonal antibody may be summarized as shown below:

(1) It is bound to a dimeric MP52.

(2) It is not bound to a monomeric MP52.

(3) The H-chain subclass thereof is γ.

(4) It is not cross-reacted with other osteogenetic factors belonging to TGF-B gene superfamily, especially TGF-β and BMP-2 having similar amino acid sequences.

Purification of human MP52 using the present monoclonal antibody may be carried out according to a conventional method. The present monoclonal antibody is adsorbed onto an adsorbent such as Sephadex (manufactured by Pharmacia). A roughly purified human MP52 solution is passed through the said adsorbent to adsorb human MP52. Next, the adsorbed human MP52 may be treated with a suitable eluent in a conventional manner to afford human MP52 of a higher purity.

The antibodies can be classified into typing by the sandwich ELISA method using the purified monoclonal antibodies (20 species of aMP-1, 2, 3, 4, 5, 6, 7, 8, 9, 10, 11, 12, 13, 14, 15, 16, 18, 20, 21, and 22) and the each HRPO-labelled monoclonal antibodies.

As a result, the monoclonal antibodies differing in specificity to 10 species of epitopes were identified. They were classified as types A, B, C, D, E, F, G, H, I, and J as indicated.

The rat osteoblastic cell line ROB/C26 is known to possess a receptor for the human MP52. It is known that when the human MP52 is added to the culture of this cell line, the activity of the alkaline phosphatase (ALP) is elevated. When the purified monoclonal antibodies are added to the culture and if they inhibit the ALP activity, it can be determined to inhibit the biological activity of human MP52.

As a result, the species of aMP-4, 5, 8, 11, 20 and 21 were recognized to manifest a strong inhibiting activity. Of the species thus tested, aMP-4 and aMP-5 were antibodies that reacted specifically with the D-rhMP52 and, therefore, were judged to be monoclonal antibodies which were capable of substantially inhibiting the MP52/MP52 receptor binding under physiological conditions.

Quantitation of human MP52 using the present monoclonal antibody can be performed by a well-known ELISA method. Specific examples thereof are also disclosed as examples in the present specification. Quantitation of human MP52 can be performed at a sensitivity of as low as 42.4 pg/ml.

BRIEF EXPLANATION OF THE DRAWINGS

FIGS. 3A-1 and 3A-2 and FIGS. 3B-1 and 3B-2 are a photograph of Western blotting analytic diagram on reactivity of the present monoclonal antibody to a monomeric rhMP52 (A) and a dimeric rhMP52 (B).

BEST MODE FOR ENABLEMENT OF THE INVENTION

The present invention is illustrated by the following references and examples.

Reference 1 Preparation of rhMP52

1. Construction of expression vector (1) Isolation of a mature region of MP52

A mature region of human MP52 cDNA was PCR-amplified using the plasmid vector (pSK52s) containing cDNA described in W093/16099 as a template DNA.

In accordance with the process for increasing a productivity of the target proteins reported by M. Nobuhara, et al. (Agric. Biol. Chem., 52(6), 1331–1338, 1988), a part of DNA of the mature region of MP52 gene was substituted with a designed DNA sequence that permits no alternation of amino acid sequence encoded in the DNA sequence to increase the AT content around the ATG initiation codon.

The reconstruction was introduced by PCR method using the designed upstream PCR primer encompassing the mutation of SEQ ID No.:2 of the Sequence Listing. For the DNA sequence of the PCR primers were used the DNA in the SEQ ID No.:2 as an upstream primer, and the DNA in SEQ ID No.:3 of the Sequence Listing as a downstream primer.

The PCR was performed by adding the template DNA (10 ng), 50 pmols each of the PCR primers in an order direction and in a reverse direction, dNTP (0.2 mmol) and $MgCl_2$ (1.5 mmol) in the same test tube, together with Taq DNA polymerase (5 U).

Thirty cycles of PCR were performed; the conditions of each cycle were 94° C. for a minute for denaturation, 55° C. for a minute for primer annealing, and 72° C. for 2 minutes for primer extension.

The products obtained from the PCR was isolated by electrophoresis in 1.5% low melting point agarose (FMC), and the fragments of about 360 bp were isolated (Fragment 1).

(2) Construction of E. coli expression vector for the protein of the invention

Figure 1:
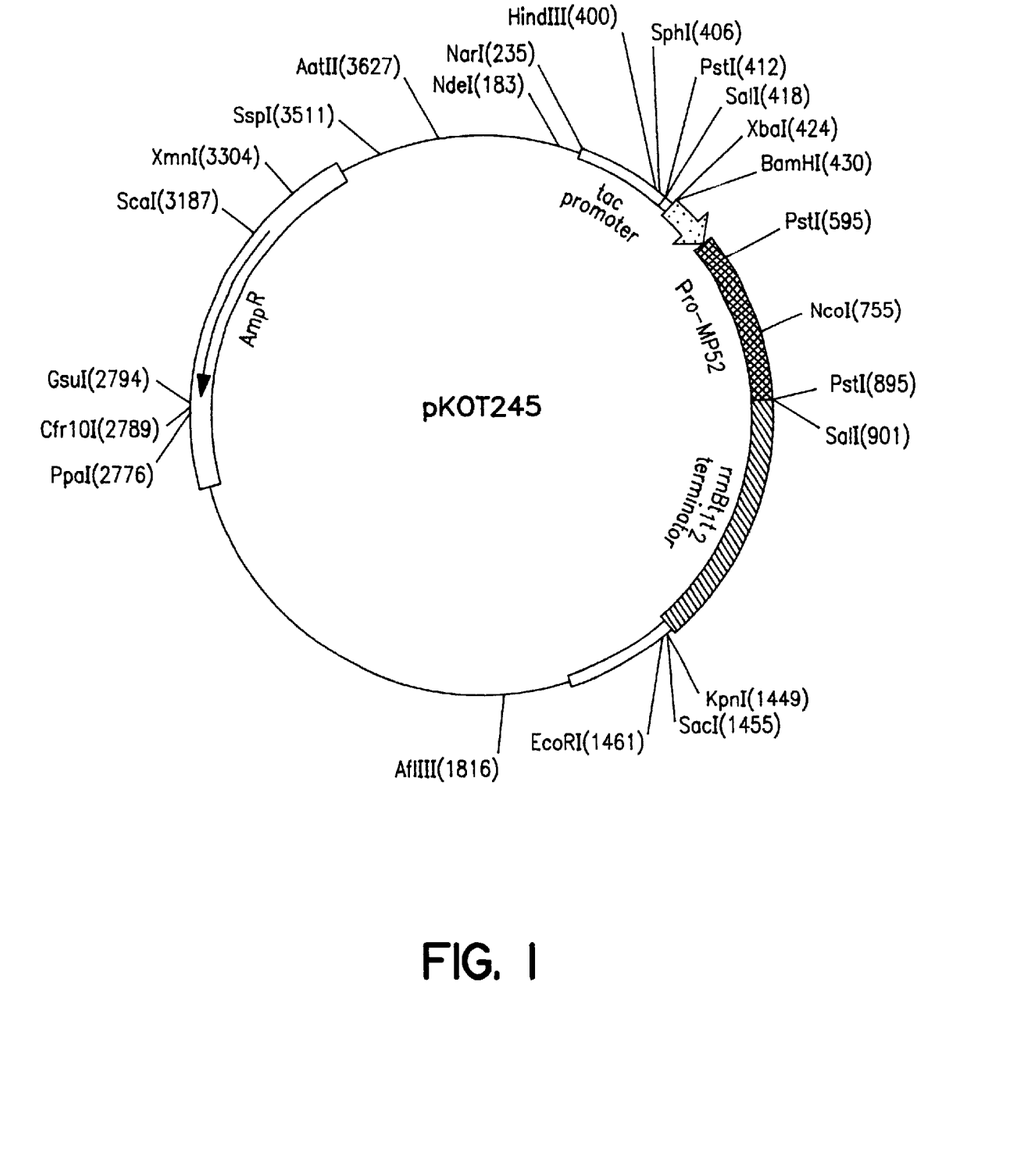
FIG. 1 is a plasmid map of the rhMP52 expression vector (pKOT245) obtained by Reference 1 (2).

In order to increase a copy number of the plasmid per bacteria, the ori region for replication origin was changed from that of pBR to pUC vector. The tac promoter region was isolated from E. coli expression vector pKK223-3 available in the market (purchased from Pharmacia Biotech) by digestion with restriction endonucleases SspI and EcoRI, treated with Mung Bean Nuclease (Takara Shuzo, Catalogue No. 2420A), ligated to the starting codon of Fragment 1 by T4 DNA Ligase (Takara Shuzo, Catalogue 2011A). The rrnBT$_1$T$_2$ terminator region of pKK223-3 was isolated by digestion with restriction endonucleases SalI and SspI, ligated with the end codon of Fragment 1 digested by SalI. Then it was ligated into the SmaI site of pUC18 vector to construct the expression vector {pKOT245 (Accession No. BIKOKEN-KI FERM BP-5499)} (FIG. 1) for the production of the protein. The length of pKOT245 is 3.7 kb. The nucleotide sequence of the expression vector constructed for the protein was analyzed by Pharmacia ALF DNA sequencer.

(3) Transformation

Transformation was performed according to the rubidium chloride transformation method by Kushner et al. (Genetic Engineering, p. 17, Elsevier, 1978). Briefly, pKOT245 was used to transform the host strain E. coli W3110M according to the method described above to produce E. coli transformants for the production of the protein.

2 Cultivation (1) Cultivation

The E. coli expressing the protein of the invention were precultured in the modified SOC medium (Bacto tryptone 20 g/l, Bacto yeast extract 5 g/l, NaCl 0.5 g/l, $MgCl_2$, $6H_2O$ 2.03 g/l, Glucose 3.6 g/l). 100 ml of the bacteria suspension was used to inoculate 5 l of the production medium (Bacto tryptone 5 g/l, Citric acid 4.3 g/l, $K_2HPO_4$ 4.675 g/l, $KH_2PO_4$ 1.275 g/l, NaCl 0.865 g/l, $FeSO_4.7H_2O$ 100 mg/l, $CuSO_4.5H_2O$ 1 mg/l, $MnSO_4.nH_2O$ 0.5 mg/l, $CaCl_2.2H_2O$ 2 mg/l, $Na_2B_4O_7. 10H_2O$ 0.225 mg/l, $(NH_4)6Mo_7O_{24}$ 0.1 mg/l, $ZnSO_4.7H_2O$ 2.25 mg/l, $CoCl_2.6H_2O$ 6 mg/l, $MgSO_4.7H_2O$ 2.2 g/l, Thiamine HCl 5.0 mg/l, Glucose 3 g/l), which was cultured in a 10 liter fermentor with aeration-agitation, and then upon reaching the early stage of logarithmic growth phase ($OD_{550}$=5.0), isopropyl-β-D-thiogalactopyranoside at a final concentration of 1 mM was added and the cultivation was continued until reaching $OD_{550}$=150. During the cultivation, temperature was kept at 32° C., and pH at 7.15 by adding ammonia. In order to prevent lowering of a dissolved oxygen concentration, an agitation was sped up to keep the dissolved oxygen concentration at 50% of air saturation. The cultivation was proceeded by adding 50% glucose solution at a level of 0.2% to obtain a high cell density, with an indication of abrupt increase of the dissolved oxygen concentration.

(2) Preparation of E. coli inclusion bodies

The culture broth obtained by the method described above was centrifuged to harvest the cells, which were then suspended in 25 mm Tris-HCl buffer containing 10 mM ethylene diamine tetraacetic acid (pH 7.3). The cells were disrupted by passing through a homogenizer (made by APV Gaulin Inc.) and centrifuged again to harvest the precipitate containing the inclusion bodies.

3 Purification (1) Solubilization of E. coli inclusion bodies

After washing with 1% Triton X-100 three times, the E. coli inclusion bodies were centrifuged at 3,000×g for 30 minutes at 4° C., and then the resultant precipitate was solubilized by sonicating with 20 mM Tris-HCl buffer, pH 8.3, 8 M urea, 10 mM DTT, and 1 mM EDTA.

(2) Preparation of monomers

The solubilized solution was centrifuged at 20,000×g for 30 minutes at 4° C. and the resultant supernatant was collected. The obtained supernatant was subjected to SP-Sepharose FF (Pharmacia AB) equilibrated with 20 mM Tris-HCl buffer pH 8.3, 6 M urea, and 1 mM EDTA, and then, after washing with the same solution, it was eluted with the same solution containing 0.5 M NaCl. To the eluate were added $Na_2SO_3$ and $Na_2S_4O_6$ to reach the final concentration respectively at 111 mM and 13 mM and then sulfonated at 4° C. for 15 hours. The sulfonated solution was gel-filtrated on Sephacryl S-200 (Pharmacia AB) equilibrated with 20 mM Tris-HCl buffer, pH 8.3, 6 M urea, 0.2 M NaCl, and 1 mM EDTA to obtain purified sulfonated monomers of the protein of the invention.

(3) Refolding

The solution of the sulfonated monomers was added into a 9 times volume of 50 mM Na-Glycine buffer pH 9.8, 1 MNaCl, 30 mm CHAPS, 5 mM EDTA, 2 mM GSH (reduction type glutathione), and 1 mM GSSG (oxydation type glutathione) with stirring, and then incubated for 3 days at 4° C. to oxidize and refold the protein of the invention.

(4) Preparation of homodimers

The refolded MP52 was loaded on RESOURCE RPC column (Pharmacia AB) of a reverse-phase HPLC preequilibrated with 25% acetonitrile containing 0.05% TFA, and then eluted with a linear gradient of 25–45% acetonitrile containing 0.05% TFA. The eluate was monitored at 280 nm absorbance. The homodimer protein fractions were collected and lyophilized. The sample was gel-filtrated by Sephacryl S-200 equilibrated with 20 mM Tris-phosphate buffer of pH 8.0 containing 0.8 M urea and 1 M NaCl, and then the fraction of homodimer protein was collected using reverse-phase HPLC by the same manner as above described.

(5) Determination of physicochemical properties of the purified protein of the invention a) Analysis of N-terminal amino acid sequence Analysis of the N-terminal amino acid sequence for the purified proteins was performed using an amino acid sequencer Model 476A (Applied Biosystems Inc.) to confirm the amino acid sequence from the N-terminal to the 30th amino acid sequence as shown in SEQ ID No.:1 of the Sequence Listing.

b) Analysis of amino acid composition

The analysis of amino acid composition of the purified proteins obtained above was performed by an amino acid sequencer (PICO TAG Systems, Waters). The result was shown in Table 1. The number described in Table 1 indicates the number of amino acid residue per a monomer protein.

TABLE 1

| Amino acid | Practical number | Expected number |
|---|---|---|
| Asx | 11.5 | 12 |
| Glx | 10.9 | 11 |
| Ser | 8.4 | 9 |
| Gly | 4.3 | 4 |
| His | 4.0 | 4 |
| Arg | 7.7 | 7 |
| Thr | 5.4 | 6 |
| Ala | 7.3 | 7 |
| Pro | 10.2 | 10 |
| Tyr | 2.9 | 3 |
| Val | 5.7 | 7 |
| Met | 5.1 | 4 |
| ½Cys | 2.6 | 7 |
| Ile | 4.9 | 6 |
| Leu | 10.0 | 10 |
| Phe | 4.0 | 4 |
| Lys | 5.9 | 6 |
| Typ | — | 2 |
| length of the sequence | | 119 |

—: undetectable c) Analysis by electrophoresis

Molecular weight of the purified proteins obtained above was confirmed to be about 28 KDa on SDS-PAGE electrophoresis under non-reducing conditions.

From the results shown in the above a), b) and c), it is found that the protein of the invention comprises 119 amino acid residues starting from the N-terminal Pro singly.

Reference 2 Production of CHO-MP52

(1) Construction of expression vector for CHO-MP52

Figure 2:
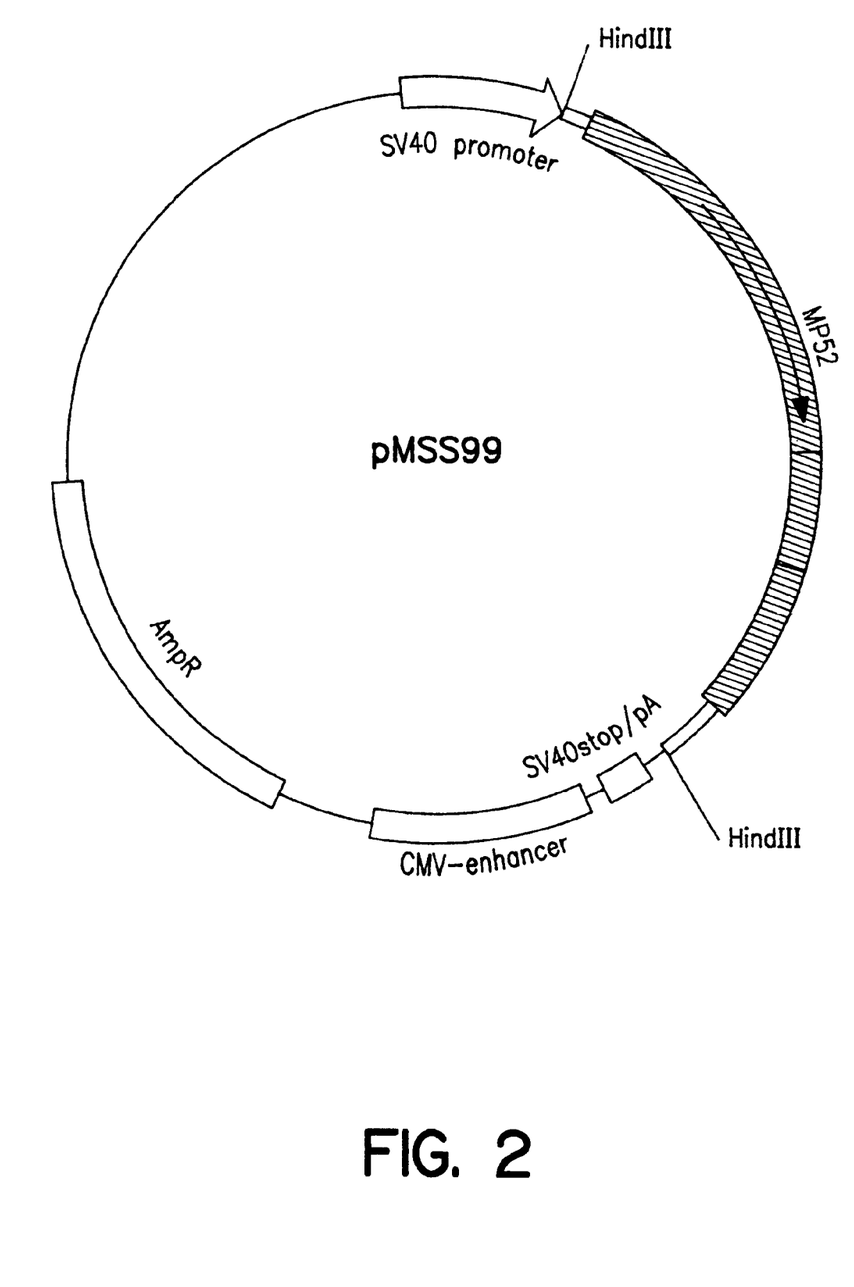
FIG. 2 is a plasmid map of the CHO-MP52 expression vector pMSS99 (5.0 kb). The CHO-MP52 DNA base sequence is nucleotides from 576 to 2297 as shown in SEQ ID NO:4 of the Sequence Listing.
Figure 3A:
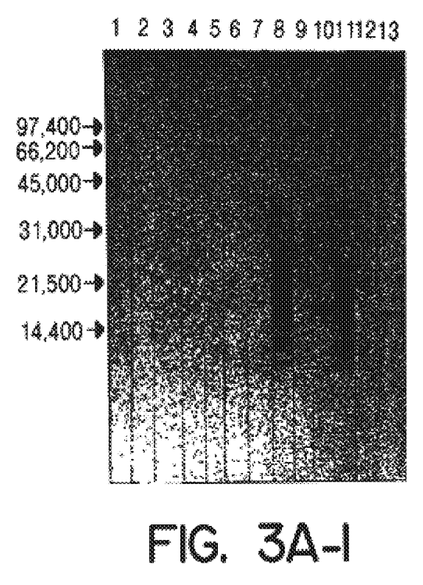
Figure 3A:
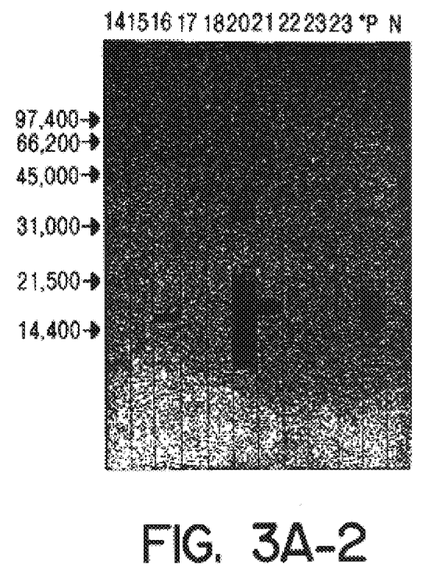
Figure 3B:
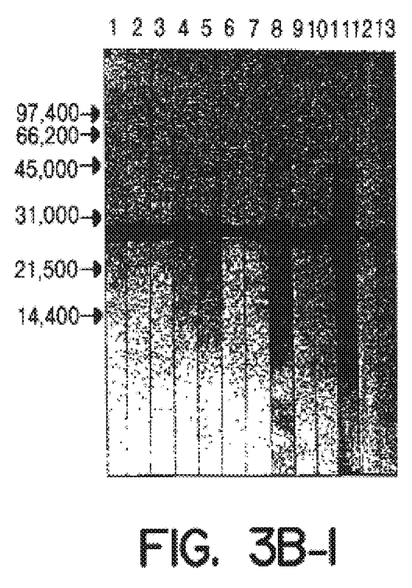
Figure 3B:
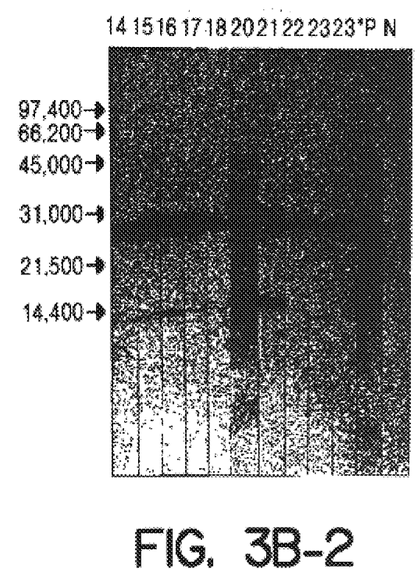

The pSK52s vector containing human MP52 gene, which was supplied by Dr. Hötten of Biopharm GmbH, was digested with HindIII and DNA fragment containing human MP52 gene was isolated by the extraction from 0.8% low melting agarose gels and ligated into the HindIII site of pABstop vector, which is supplied by Dr. Gerd Zettlmeissl of Behringwerke AG. The structure of the CHO-MP52 expression vector, pMSS99 (5.0 kb) as shown in FIG. 2, was confirmed by the DNA sequencing and the restriction enzyme mapping. The CHO-MP52 DNA sequence in pMSS99 was the nucleotides from the 576th to the 2279th shown in the SEQ ID NO:4 of the Sequence Listing.

(2) Establishment of CHO clones producing CHO-MP52

CHO-DUKX-B11 cells, mutants of CHO cells, which were provided by Dr. Zettlmeissl of Behringwerke AG, were cotransfected with pMSS99 and pSVOAdhfr which was also provided by Dr. Zettlmeissl, by calcium phosphate-mediated DNA transfer method. Then high producer clones of CHO-MP52 were established by gene amplification protocol using methotrexate (MTX).

Ten µg of pMSS99 and 2 µg of pSVOAdhfr were dissolved in 1 ml of 25 mM HEPES-140 mM NaCl-0.75 mM $Na_2HPO_4$ (pH 7.05), then mixed with 50 µl of 2.5 M $CaCl_2$. The resultant precipitates were overlaid to CHO-DUKX-B11 cells in a 10 cm dish and stood at room temperature for 30 min. Then 8 ml of MEM ALPHA with ribo- and deoxyribo-nucleosides (MEMα+) containing 10% fetal bovine serum (FBS) was added to the cell layer to incubate in a $CO_2$ incubator for 4–6 h. After the treatment with 10% glycerol in MEMα+ containing 10% FBS at room temperature for 3 min, the cells were cultured in MEMα+ containing 10% FBS for 2 days. Then the cells were replaced in MEM ALPHA without ribo- and deoxyribonucleosides (MEMα−) containing 10% dialyzed FBS to select the transformants. The transformant clones were isolated and assayed for the expression of CHO-MP52 by Western blotting analysis as described in the next session.

The CHO-MP52 producing clones were further selected stepwisely in increasing concentrations of methotrexate (MTX) to amplify the MP52 gene in accordance with the pSVOAdhfr gene. Several clones were obtained to produce 1–3 µg of CHO-MP52/$10^6$ cells/24 h at 400 nM MTX.

(3) Detection of CHO-MP52 in the culture supernatants

Clones were examined for the expression of CHO-MP52 by Western blotting analysis as follows: the culture supernatants (1–15 µl) were applied on SDS-PAGE (15–25% polyacrylamide gradient gel, Daiichi Pure Chemicals) under reducing conditions, then the proteins were transferred to a PVDF membrane (Clear Blot Membrane-P, ATTO). The membrane was blocked with Block Ace (Dai-Nihon Seiyaku) for 1 h, rinsed with Tris-buffered saline (TBS), then treated with 10 µg/ml of chicken antibodies to CHO-MP52 in 10-times diluted Block Ace overnight. After washing the membrane with 0.1% Tween 20 in TBS (TTBS), the membrane was treated with rabbit anti-chicken IgG-ALP conjugate (Sigma A 9171) in 10-times diluted Block Ace for 1 h. The membrane was washed with TTBS, then, reacted with Alkaline phosphatase Conjugate Substrate Kit (BIO-RAD) to visualize the bands corresponding to MP52.

(4) Cell culture of the CHO-MP52-producing CHO cell line

The CHO cell line with the highest productivity of CHO-MP52, MC-2 (Deposit No. FERM BP-5142), was grown with roller bottles containing MEMα- supplemented with 10% FBS, 400 nM MTX, 100 U/ml Penicillin, 100 µg/ml Streptomycin. After the MC-2 cells were up to confluency, they were washed with serum-free MEMα- and then cultured in serum-free DME/F12 supplemented with 10 mM HEPES (pH 7.3), 10 KIU Aprotinin, 1 mM sodium butyrate, 6 µg/ml sodium selenate, 5 µg/ml transferrin, 18 µg/ml ethanol amine, 9 µg/ml insulin, 100 U/ml Penicillin, 100 µg/ml Streptomycin. The conditioned medium was collected every day for a week.

(5) Purification of CHO-MP52

The CHO culture supernatant and 0.1 vol. of 0.2 M sodium phosphate buffer, pH 6.0, were mixed and applied to POROS HS column (10 ml, PerSeptive Biosystems) previously equilibrated with 50 mM NaCl, 20 mM sodium phosphate buffer, pH 6.0. The proteins were eluted by linear gradient of NaCl from 0.05 to 2 M and collected with 20 of 10 ml fractions. The eluted MP52s were observed as three types of monomers and their apparent molecular weights were determined about 52, 40 and 14 kD by SDS-PAGE analysis under reducing conditions. These monomers form three types of homodimers (104 kD, 80 kD and 28 kD) and three types of heterodimers (92 kD: 40 kD-52 kD, 66 kD: 14 kD-52 kD, and 54 kD: 14 kD-40 kD) and all those dimers were named CHO-MP52 except 28 kD homodimer which seemed to be known as a mature homodimer of human MP52 (WO 95/04819). Therefore, 104 kD homodimer and 80 kD homodimer were isolated from the above fractions to examine the N-terminal amino acid sequences and the biological activities.

The fractions from 5th to 9th were pooled and concentrated about 10 fold. The concentrate was loaded to Superdex 200 pg (1.6 I.D.×60 cm, Pharmacia) previously equilibrated with 20 mM sodium phosphate buffer, pH 7.1, containing 1 M NaCl. The elution was performed at the flow rate of 0.5 ml/min. The fractions containing the 104 kD homodimer and the fractions containing the 80 kD homodimer were pooled separately. Each was applied to reverse-phase HPLC column (RESOURCE RPC, 3 ml, Pharmacia) and these were eluted at 35–40 % acetonitrile. The concentrations of the isolated CHO-MP52 were determined by densitometory of the bands of proteins on SDS-PAGE gel.

The N-terminal amino acid sequence analysis was performed using a pulse liquid gas phase sequencer (Applied Biosystems model 476) for 80 kD homodimer and 104 kD homodimer, respectively. The results are shown in table 2.

TABLE 2

| HMW MP52s | N-terminal amino acid |
|---|---|
| 80 kD | Lys Ala Arg Glu Pro Gly Pro Pro Arg Glu Pro |
| | Ala Arg Glu Pro Gly Pro Pro Arg Glu Pro |
| | Lys |
| 104 kD | Ala Pro Asp Leu Gly Gln Arg Pro Gln Gly Thr |

The amino acid sequences 80 kD were from Lys 121 or Ala 122 to Arg 474 and that of 104 kD was from Ala 1 to Arg 474 in SEQ ID NO. :4 of the Sequence Listing. It was newly found that the CHO cells produced 3 types of homodimers, 104 kD, 80 kD and 28 kD, and 3 types of heterodimers, namely diners of 92 kD, 66 kD and 54 kD.

EXAMPLE 1

1. Preparation of antigen and method for sensitization

A dimer type (hereinafter referred to briefly as "D-rhMP52," as described specifically in Reference 1) was expressed by E. coli (Deposit No. FERM BP-5499) with a plasmid (pKOT245) including a cDNA coding for the amino acid sequence of human MP52 and constituted by oxidizing a monomer type rhMP52 obtained by solubilizing the inclusion body thereof by the standard method. The D-rhMP52 was passed through such refining processes as the isoelectric precipitation and the gel permeation to obtain the rhMP52 at the ultimate concentration of about 0.5 mg/ml. This purified rhMP52 was used as an antigen. Otherwise, a dimer type (hereinafter referred to briefly as "CHO-MP52," as described specifically in Reference 2) was expressed by a CHO cell (Deposit No. FERM BP-5142) and used at the concentration mentioned above as an antigen. The production of an immunized mouse was effected by intraperitoneal injection into a BALB/c mouse 70, 20, 10, and 52 μg of the emulsion prepared by solving the CHO-MP52 (containing not less than 80% of an incompletely processed precursor) in an aqueous 10 mM hydrochloric acid solution and mixing the resultant solution with a complete Freund's adjuvant (CFA) at a ratio of 1:1 respectively on the 0th, 7th, 16th, and 112th day and 18 μg of the emulsion of the MP52 (containing a monomer slightly) prepared similarly on the 29th day and, after an interval of about one month, 50 μg of the emulsion prepared by mixing a solution containing the D-rhMP52 with an incomplete Freund's adjuvant (IFA) at a rate of 1:1. To the mouse thus continually sensitized six times, 60 μg of the D-rhMP52 was subcutaneously administered without using an adjuvant on the 42nd day after the final injection and, after an interval of 42 days (3 days before fusion of cell), 50 μg of the D-rhMP52 was intravenously administered through the tail vein.

EXAMPLE 2

Cell fusion

After 3 days following the final immunization, the spleen was excited from the sensitized mouse and spleen cells were prepared. The spleen cells thus obtained were mixed with a murine myeloma cell strain (SP2/0) at a ratio of 10:1, the resultant mixture was centrifuged at 1500 rpm, and the cell pellets were slowly loosed as kept warmed in 40% polyethylene glycol (PEG1500) at 37° C. The loosed cell pellets were gently stirred by the tip of a pipet while 1 ml of a RPMI 1640 culture medium excluding FCS (produced by Nissui Seiyaku K.K.) was slowly poured therein. Then, the speed of centrifugation was gradually increased from 250 rpm to 1000 rpm over a period of about 6 minutes. The pellets obtained at the end of the accelerated centrifugation were washed once with an FCS-free culture medium. Finally, the pellets were distributed among the wells of a 96-well plate with the aid of a solution prepared by adding HAT [hypoxanthine (H), aminopterin (A), and thymidine (T)] to a RPMI 1640 culture medium containing 20% of FCS so as to place 10,000 spleen cells in each well.

EXAMPLE 3

Primary screening by the ELISA method

The product of about 6,000 fused cells was tested for the ability to yield a monoclonal antibody to human MP52 by the following procedure.

1) The D-rhMP52 used for the immunization and a monomer type rhMP52 obtained by reducing the D-rhMP52 and subjecting the product of reduction to sulfonation of the SH group thereof (hereinafter referred to briefly as "M-rhMP52") to inhibit the -ss- bondage were deposited on plates (NUNC, MAXISORP), each at a concentration of 1 μg/ml, in a fixed amount of 50 μl and incubated at room temperature for one hour to coat the plates.

2) The coated plates were washed with PBS (washing liquid) containing Tween 20 and then the non-diluted culture supernatant was added thereto in a fixed amount of 50 μl per well of plate and incubated at room temperature for one hour.

3) The contents of the wells were washed three times with the washing liquid and then HRPO-labelled rabbit immunoglobulin antibodies to mouse immunogloblins (DAKO, F206) was added to the wells at a concentration of about 1 μg/ml in a fixed amount of 45 μl per well. The diluent used in this case was prepared by solving casein (produced by Kanto Kagaku K.K.) at a concentration of 2 mg/ml in a 0.1 M Tris hydroxymethyl aminomethane buffer solution (TBS, pH 7.4).

4) The wells were incubated at room temperature for one hour and washed three times with the washing liquid and, to the washed wells, a coloring liquid (Chromogen-TMB, produced by Behringwerke) was added in a fixed amount of 50 µl per well.

5) The ensuant coloring reaction was allowed to proceed at room temperature for about 5 minutes and then stopped by addition of 50 µl of 0.5 N sulfuric acid.

6) The degree of coloration was measured at an absorbance of $OD_{450}$ nm within 30 minutes after the stop of the reaction.

In a total of 23 monoclonal antibodies sequentially dubbed aMP-1 through aMP-23, the 20 monoclonal antibodies excluding aMP-17, aMP-19, and aMP-23 which failed to tolerate the subsequent cloning process were obtained. The results are shown in Table 3. In the discrimination between the positive and the negative test, the average±10 SD ($OD_{450}$nm=0.05) was used as the cutoff value. The monoclonal antibodies, aMP-1, 2, 3, 4, 5, 6, 7, 9, 12, 14, 15, 18, and 22 reacted only with D-rhMP52and the monoclonal antibodies aMP-8, 10, 11, 13, 16, 20, and 21 reacted with both D-rhMP52 and M-rhMP52. From the viewpoint of specificity, the 20 monoclonal antibodies were classified under at least two kinds of antibodies.

EXAMPLE 4
Confirmation of specificity by the Western blotting method

1) The rhMP52 (1 µg/lane/0.5 mm) was subjected to SDS-PAGE using 15–25% gradient gel (produced by Daiichi Kagakusha K.K.) under non-reducing conditions (for causing the antigen to migrate as D-rhMP52) and under reducing conditions (for causing the antigen to migrate as M-rhMP52) and then transferred (30 V, 2 h)to a nitrocellulose membrane by the standard method.

2) The nitrocellulose membrane having based the transfer was kept immersed in a TBS solution containing casein at a concentration of about 3 mg/ml for not less than 20 minutes to block a non-specific reaction.

3) The nitrocellulose membrane carrying the transferred rhMP52 thereon was incubated in the culture supernatant containing a monoclonal antibody (in the range of 4 µg/ml–40 µg/ml) by being shaken in the culture supernatant in its unmodified form at room temperature for one hour.

4) The incubated antibody was washed with a large amount of phosphate buffer solution (PBS, pH 7.2) (repeating 5 minutes' immersion in the solution three times, with the solution replaced with a new supply at the end of each immersion).

5) HRPO-labelled rabbit immunoglobulin antibodies to mouse immunogloblins were placed as a secondary antibody at a concentration of 1 µg/ml in a casein-TBS dilute solution and incubated therein at room temperature for one hour.

6) The incubated antibody was thoroughly washed in the same manner as in 4) above.

7) The washed antibody was kept immersed in a coloring agent (TrueBlue/Peroxidase substrate, produced by Kirkegaard Perry Laboratories) to undergo a coloring reaction. Then, it was thoroughly washed with running water. The results were in agreement with those of the primary screening with the ELISA. The results are shown in FIG. 3.

EXAMPLE 5
Decision of subclass of monoclonal antibody

The subclasses of a monoclonal antibody produced by the clone were decided by the use of a mouse monoclonal antibody isotyping kit, RPN29 produced by Amersham Corp. in accordance with the handling manual thereof. The subclasses of the monoclonal antibody are shown in Table 4.

All the monoclonal antibodies were found to have an L-chain subclass of K and H-chain subclass of γ1 or γ2a.

EXAMPLE 6
Confirmation of specificity

The human MP52 is a molecule which belongs to the TGF-β gene superfamily and has been found to resemble in terms of the structure and the amino acid sequence the other TGF-β gene superfamily, particularly the TGF-β2 and BMP-2. To study the monoclonal antibody of this invention and determine whether or not it would manifest specificity to the human MP52, the human recombinant TGF-β2 (rhTGFB2) and the human recombinant BMP-2 (rhBMP-2) were procured and subjected to the ELISA in the same manner as in Example 3 above to determine their specificity. The results are shown in Table 5.

All the monoclonal antibodies failed to react with the TGF-β2 and the BMP-2. Thus, they were confirmed to be antibodies specific to the MP52.

EXAMPLE 7
Purification of antibody

The purification of the monoclonal antibodies from the culture supernatant and the mouse ascitic fluids was performed by the use of the column of protein A or protein G (produced by Pharmacia) in accordance with the handling manual thereof. The column of protein A was used for purifying the antibody from the culture supernatant and the column of protein G for purifying the antibody from the ascitic fluids.

EXAMPLE 8
Secondary screening (typing) by sandwich ELISA method

1) The purified monoclonal antibodies (20 species of aMP-1, 2, 3, 4, 5, 6, 7, 8, 9, 10, 11, 12, 13, 14, 15, 16, 18, 20, 21, and 22) were each dispensed among the wells of a 96-well plate at a concentration of 1 µg/ml to coat the wells each in a fixed amount of 50 µl (one hour at room temperature).

2) After the coated wells were washed three times with a washing liquid (BEP-II, produced by Behringwerke), a solution obtained by diluting the D-rhMP52 to a prescribed concentration of 30 ng/ml with casein/TBS was dispensed in a fixed amount of 50 µl among the wells and incubated at room temperature for one hour.

3) After washing three times with washing liquid, the monoclonal antibodies shown in 1) above biotinylated in advance by the use of an antibody labeling system (produced by American Qualex Corp. and marketed under designation of "Biotinylation Kit") were diluted each to a concentration of 1 µg/ml with casein/TBS, and each biotinylated monoclonal antibodies were added to the wells of all kinds of monoclonal antibody coated in 1) above. For example, all the biotinylated species of aMP-1, 2, 3, 4, 5, 6, 7, 8, 9, 10, 11, 12, 13, 14, 15, 16, 18, 20, 21, and 22 were each reacted with the plates coated with the species of aMP-1 and all the biotinylated monoclonal antibodies were each reacted with the plates coated with the species of aMP-2–22 in the same manner as above (room temperature for one hour).

4) After washing three times with washing liquid, a HRPO-labelled AVIDIN-PEROXIDASE (produced by Sigma) was added at a concentration of 1 µg/ml to casein/TBS and incubated at room temperature for one hour.

5) After washing in the same manner as above, they were caused to undergo a coloring reaction in the same manner as in 3 and 4).

6) After incubation of 15 minutes, the reaction was stopped and the degree of color reaction were measured in the same manner as in 3), 5) and 6).

Figure 4A:
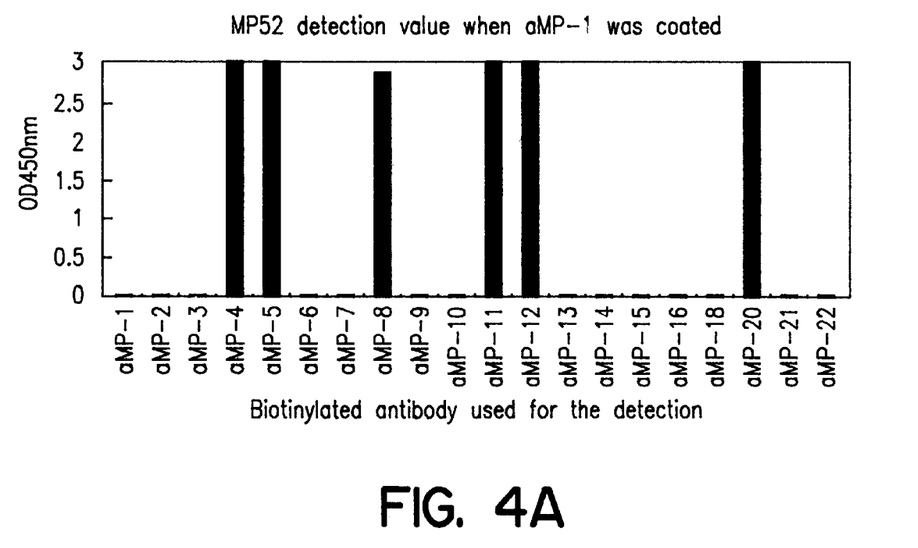
FIGS. 4A and 4B are a diagram obtained when identification (i.e. typing) of the present monoclonal antibodies was investigated. As illustrative examples are shown those antibodies coated with aMP-1 and aMP-4.
Figure 4B:
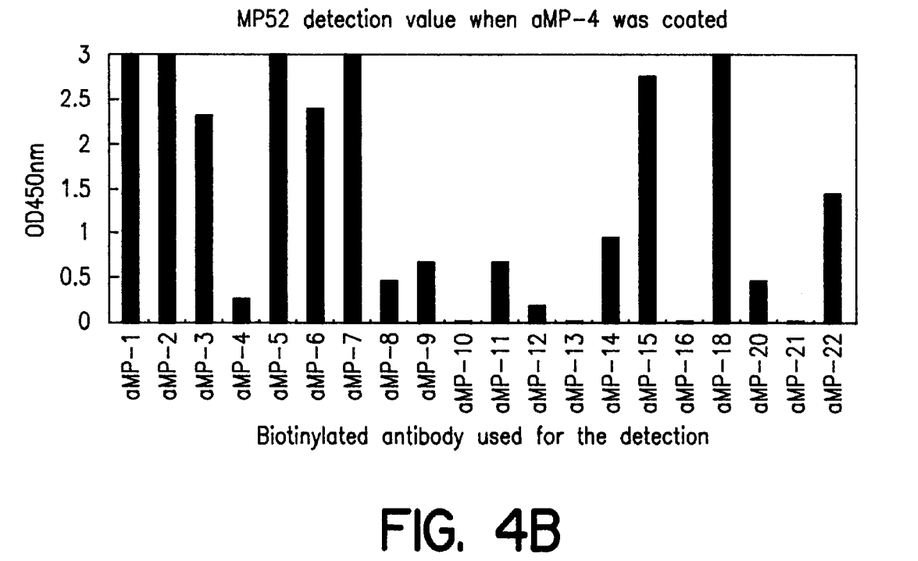

Part of the results are shown in FIG. 4. One and the same monoclonal antibody ought to produce equal results in all the combinations. The species of aMP-1 and aMP-4 shown by way of example in FIG. 4, however, were found to be entirely different antibodies. Based on these results, similarity and dissimilarity of all the monoclonal antibodies were determined. As a result, the monoclonal antibodies differing in specificity to 10 species of epitopes were identified. They were classified as types A, B, C, D, E, F, G. H. I, and J as indicated in Table 6.

EXAMPLE 9
Inhibition of biological activity of D-rhMP52 by monoclonal antibody The rat osteoblastic cell line ROB/C26 is known to possess a receptor for the human MP52. It is known that when the human MP52 is added to the culture of this cell line, the activity of the alkaline phosphatase (ALP) is elevated. When the rhMP52 was added in a prescribed amount, and all the purified monoclonal antibodies were added at the final concentration of 20 µg/ml, it was studied whether or not they would inhibit the ALP activity. When the rhMP52 was added at a concentration of 10 ng/ml to the ROB/C26 and then incubated for several days, a stimulus was conducted through the MP52 receptor on the surface of the cells and, as a result, the ALP activity was increased. The ALP activity could be quantitated by a coloring reaction caused with a substrate specific to ALP in the same manner as in the ELISA (providing that the wavelength for determination was $OD_{405}$ nm). The results are shown in Table 7. The rhMP52 alone in the absence of the antibody showed an ALP activity of 0.158 $OD_{405}$nm. This ALP activity was changed by the addition of a monoclonal antibody. The strength of the inhibiting activity of the monoclonal antibody was rated proportionately to the smallness of this change of the ALP activity. As a result, the species of aMP-4, 5, 8, 11, 20 and 21 were recognized to manifest a strong inhibiting activity. Of the species thus tested, aMP-4 and aMP-5 were antibodies that reacted specifically with the D-rhMP52 (Table 1) and, therefore, were judged to be monoclonal antibodies which, unlike the species of aMP-8, 11. 20, and 21 additionally reacting with the M-rhMP52, were capable of substantially inhibiting the MP52/MP52 receptor binding under physiological conditions. The hybridomas which yield the monoclonal antibodies aMP-4 and aMP-5 have been deposited at the Life Science Industrial Technology Research Institute of the Agency of Industrial Technology (1–3, Higashi 1-chome, Tsukuba-shi, Ibaraki, Japan), respectively, under Deposit Nos. FERM BP-5939 and FERM BP-5940.

EXAMPLE 10
Quantitation of MP52 by monoclonal antibody by sandwich ELISA method The monoclonal antibodies were classified into 10 types as described in Example 8. Out of them, a sandwich ELISA was constructed using aMP-4 of type C and aMP-5 of type D. Namely, 1) A 96 well plate is coated with 50 µl of purified aMP-5 each at the concentration of 5 µg/ml (1 h, at room temperature).

2) After washing with a washing liquid, 50 µl of purified MP52 at the concentration of 1 ng/ml at most which is diluted by casein/Tris buffer in order is added to each well. The plate is incubated for 1 h at room temperature.

3) After washing with a washing liquid, 50 µl of biotinylated purified aMP-4 antibody at the concentration of 1 µg/ml is added to each well, standing for 1 h at room temperature.

4) After washing with a washing liquid, AVIDIN-PEROXIDASE (SIGMA A-3151) at the concentration of 1 µg/ml is added, standing for 1 h at room temperature.

5) After washing with a washing liquid, the ensuant coloring reaction is allowed to proceed by the same manner as shown as 3) and 4).

6) After 30 minutes, the ensuant coloring reaction is stopped by addition of 50 µl of 0.5 N sulfuric acid.

7) The degree of coloration was measured at an absorbance of $OD_{450}$nm after the stop of the reaction.

Figure 5:
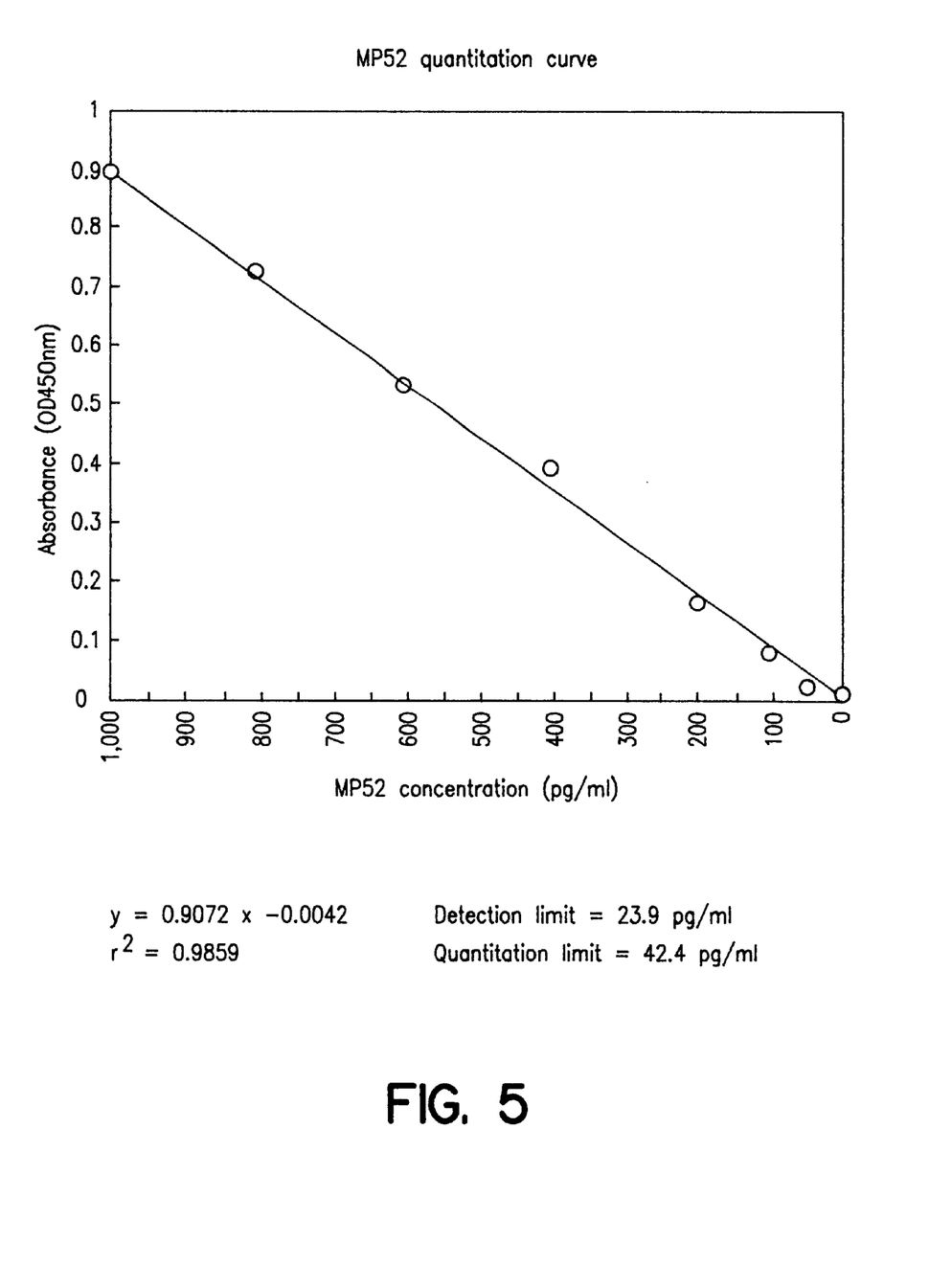
FIG. 5 is a diagram showing quantitation curves for MP52 using the present monoclonal antibody.

The results are shown in FIG. 5. The detection limit was about 23.9 pg/ml and the quantitation limit was 42.4 pg/ml.

In this specification, the detection limit means a concentration of MP52 which is significantly higher than that of the solution without MP52 as a background concentration, and the quantitation limit means the lowest concentration of MP52 which is detected with reliability.

TABLE 3

Result of the anti-MP52 antibody titer detected by ELISA

| Monoclonal antibody | Antigen used | |
|---|---|---|
| | Monomer rhMP52 | Dimer rhMP52 |
| aMP-1 | 0.03 | 1.35 |
| aMP-2 | 0.01 | 1.03 |
| aMP-3 | 0.01 | 0.92 |
| aMP-4 | 0.01 | 1.58 |
| aMP-5 | 0.01 | 1.03 |
| aMP-6 | 0.01 | 0.96 |
| aMP-7 | 0.01 | 1.53 |
| aMP-8 | 1.89 | 1.98 |
| aMP-9 | 0.04 | 1.15 |
| aMP-10 | 1.08 | 1.78 |
| aMP-11 | 1.81 | 1.95 |
| aMP-12 | 0.02 | 0.33 |
| aMP-13 | 0.26 | 1.48 |
| aMP-14 | 0.03 | 1.26 |
| aMP-15 | 0.01 | 1.35 |
| aMP-16 | 0.06 | 1.58 |
| aMP-18 | 0.01 | 1.19 |
| aMP-20 | 1.85 | 2.01 |
| aMP-21 | 1.41 | 1.86 |
| aMP-22 | 0.01 | 0.88 |
| anti-MP52 antiserum | 1.83 | 2.23 |
| negative control | 0.01 | 0.01 | unit: $OD_{450}$nm
cut-off value: 0.05

TABLE 4

Subclass of monoclonal antibody

| Monoclonal antibody | Subclass | |
|---|---|---|
| | H-chain | L-chain |
| aMP-1 | γ1 | κ |
| aMP-2 | γ1 | κ |
| aMP-3 | γ1 | κ |
| aMP-4 | γ2a | κ |
| aMP-5 | γ1 | κ |
| aMP-6 | γ1 | κ |
| aMP-7 | γ2a | κ |
| aMP-8 | γ1 | κ |
| aMP-9 | γ1 | κ |
| aMP-10 | γ1 | κ |
| aMP-11 | γ1 | κ |
| aMP-12 | γ1 | κ |
| aMP-13 | γ1 | κ |
| aMP-14 | γ2a | κ |
| aMP-15 | γ1 | κ |
| aMP-16 | γ1 | κ |

TABLE 4-continued

Subclass of monoclonal antibody

| Monoclonal antibody | Subclass | |
|---|---|---|
| | H-chain | L-chain |
| aMP-18 | γ1 | κ |
| aMP-20 | γ1 | κ |
| aMP-21 | γ1 | κ |
| aMP-22 | γ2a | κ |

TABLE 5

Specificity of monoclonal antibody

| Monoclonal antibody | Antigen used | |
|---|---|---|
| | rhTGFβ2 | rhBMP-2 |
| aMP-1 | 0.016 | 0.06 |
| aMP-2 | 0.014 | 0.043 |
| aMP-3 | 0.047 | 0.055 |
| aMP-4 | 0.046 | 0.048 |
| aMP-5 | 0.018 | 0.024 |
| aMP-6 | 0.029 | 0.018 |
| aMP-7 | 0.026 | 0.03 |
| aMP-8 | 0.034 | 0.032 |
| aMP-9 | 0.011 | 0.032 |
| aMP-10 | 0.019 | 0.028 |
| aMP-11 | 0.019 | 0.027 |
| aMP-12 | 0.012 | 0.018 |
| aMP-13 | 0.035 | 0.035 |
| aMP-14 | 0.022 | 0.024 |
| aMP-15 | 0.015 | 0.023 |
| aMP-16 | 0.023 | 0.028 |
| aMP-18 | 0.035 | 0.025 |
| aMP-20 | 0.025 | 0.018 |
| aMP-21 | 0.029 | 0.019 |
| aMP-22 | 0.025 | 0.02 |
| anti-TGFβ antibody | 2.2 | 0.025 |
| anti-BMP-2 antiserum | 1.5 | 1.351 |
| negative control | 0.076 | 0.065 | unit: $OD_{450}$nm
cut-off value: negative control value

TABLE 6

Classification of monoclonal antibody

| Type | Monoclonal antibody reacted with the same epitope |
|---|---|
| A | aMP-1, aMP-15 |
| B | aMP-2, aMP-3. aMP-6, aMP-7, aMP-18 |
| C | aMP-4 |
| D | aMP-5 |
| E | aMP-8, aMP-11, aMP-20 |
| F | aMP-9, aMP-14 |
| G | aMP-10, aMP-21 |
| H | aMP-12 |
| I | aMP-13, aMP-16 |
| J | aMP-22 |

TABLE 7

ALP activity inhibition test by monoclonal antibody

| Monoclonal antibody added | ALP activity |
|---|---|
| aMP-1 | 0.098 |
| aMP-2 | 0.125 |
| aMP-3 | 0.143 |
| aMP-4 | 0.014 |
| aMP-5 | 0.022 |
| aMP-6 | 0.142 |
| aMP-7 | 0.027 |
| aMP-8 | 0.021 |
| aMP-9 | 0.04 |
| aMP-10 | 0.045 |
| aMP-11 | 0.009 |
| aMP-12 | 0.114 |
| aMP-13 | 0.06 |
| aMP-14 | 0.079 |
| aMP-15 | 0.07 |
| aMP-16 | 0.077 |
| aMP-18 | 0.092 |
| aMP-20 | 0.016 |
| aMP-21 | 0.018 |
| aMP-22 | 0.139 |
| without antibody | 0.158 | unit: $OD_{405}$nm
listed value: practical value minus control value without MP-52 listed value: practical value minus control value without MP-52

INDUSTRIALLY APPLICABLE

The mouse anti-human MP52 monoclonal antibody of the present invention is useful for useful in, for example, purifying or assaying human MP52 produced by genetic engineering techniques.

We claim:

1. A mouse anti-human MP52 monoclonal antibody which binds to a dimeric human MP52 but not to a monomeric human MP52.

2. A mouse monoclonal antibody with the characteristics:
   (1) it is bound to a dimeric MP52,
   (2) it is not bound to a monomeric MP52,
   (3) the H-chain subclass thereof is γ,
   (4) it is not cross-reacting with other osteogenetic factors belonging to TGB-β gene superfamily having similar amino acid sequences.

3. The mouse monoclonal antibody as claimed in claim 1, wherein said monoclonal antibody binds to the human MP52 receptor binding site.

4. The mouse anti-human MP52 monoclonal antibody as claimed in claim 1, wherein said monoclonal antibody is aMP-4 (Deposit No. FERM BP-5939).

5. The mouse anti-human MP52 monoclonal antibody as claimed in claim 1, wherein said monoclonal antibody is aMP-5 (Deposit No. FERM BP-5940).

6. A hybridoma capable of producing the mouse anti-human MP52 monoclonal antibody as claimed in claim 1.

7. A method of purification of a dimeric human MP52 comprising incubating host cells having integrated therein cDNA encoding dimeric human MP52 to produce dimeric human MP52, purifying the dimeric human MP52 by binding with a mouse monoclonal antibody of claim 1 and separating dimeric human MP52.

8. The method of claim 7 wherein the mouse monoclonal antibody is that of claim 4.

9. The method of claim 7 wherein the mouse monoclonal antibody is that of claim 5.

10. In an assay method of detecting the presence of a dimeric human MP52 by binding with an anti-human MP52 monoclonal antibody, the improvement comprising using mouse anti-human antibody of claim 1 as non-human antibody.

11. In an assay method of detecting the presence of a dimeric human MP52 by binding with an anti-human MP52 monoclonal antibody, the improvement comprising using mouse anti-human antibody of claim 4 as non-human antibody.

12. In an assay method of detecting the presence of a dimeric human MP52 by binding with an anti-human MP52 monoclonal antibody, the improvement comprising using mouse anti-human antibody of claim 5 as non-human antibody.

13. The hybridoma capable of producing the monoclonal antibody as claimed in claim 4.

* * * * *